(12) United States Patent
Zimmerman

(10) Patent No.: US 10,444,149 B2
(45) Date of Patent: Oct. 15, 2019

(54) FLUORESCENT COMPOUNDS AS SENSING AGENTS

(71) Applicant: OHIO NORTHERN UNIVERSITY, Ada, OH (US)

(72) Inventor: Jake R. Zimmerman, Ada, OH (US)

(73) Assignee: Ohio Northern University, Ada, OH (US)

(*) Notice: Subject to any disclaimer, the term of this patent is extended or adjusted under 35 U.S.C. 154(b) by 192 days.

(21) Appl. No.: 15/440,879

(22) Filed: Feb. 23, 2017

(65) Prior Publication Data

US 2017/0241969 A1    Aug. 24, 2017

Related U.S. Application Data

(60) Provisional application No. 62/299,321, filed on Feb. 24, 2016.

(51) Int. Cl.
| | | |
|---|---|---|
| *G01N 21/00* | (2006.01) | |
| *G01N 21/64* | (2006.01) | |
| *G01N 33/18* | (2006.01) | |
| *G01N 33/20* | (2019.01) | |
| *C09B 13/06* | (2006.01) | |
| *G01N 33/50* | (2006.01) | |
| *G01N 31/22* | (2006.01) | |
| *C02F 1/62* | (2006.01) | |
| *C02F 101/20* | (2006.01) | |

(52) U.S. Cl.
CPC ............. *G01N 21/64* (2013.01); *C09B 13/06* (2013.01); *G01N 33/1813* (2013.01); *G01N 33/20* (2013.01); *C02F 1/62* (2013.01); *C02F 2101/20* (2013.01); *G01N 31/22* (2013.01); *G01N 33/5014* (2013.01)

(58) Field of Classification Search
CPC .................................................... G01N 33/1813
USPC ............................................................. 436/80
See application file for complete search history.

(56) References Cited

U.S. PATENT DOCUMENTS

| | | | |
|---|---|---|---|
| 4,812,409 A * | 3/1989 | Babb | .......................... C09B 3/00 435/18 |
| 5,094,944 A | 3/1992 | Hayes | |
| 7,749,765 B2 | 7/2010 | Demas et al. | |
| 8,183,049 B2 | 5/2012 | Kayano et al. | |

(Continued)

FOREIGN PATENT DOCUMENTS

EP    1035412 A2    9/2000

OTHER PUBLICATIONS

Kaur et al. "Nano molar detection of Al3+ in aqueous medium and acidic soil using chromone based fluorescent organic nanoparticles (FONPs)" Anal. Methods, 2014, 6, 8752 (Year: 2014).*

(Continued)

*Primary Examiner* — Christine T Mui
*Assistant Examiner* — Emily R. Berkeley
(74) *Attorney, Agent, or Firm* — Vorys, Sater, Seymour and Pease LLP; Mark A. Watkins, Esq.

(57) ABSTRACT

A method may comprise: exposing a substituted chromone dissolved in a solvent to a sample; taking a fluorescence measurement of the sample after exposure to the substituted chromone; and determining a presence or absence of one or more ions in the sample, a concentration of the one or more ions in the sample, or both based on the fluorescence measurement.

17 Claims, 8 Drawing Sheets

(56) References Cited

U.S. PATENT DOCUMENTS

| | | |
|---|---|---|
| 8,247,551 B2 | 8/2012 | Basu et al. |
| 8,679,849 B2 | 3/2014 | Zhang et al. |
| 2002/0018997 A1 | 2/2002 | Remedios et al. |
| 2007/0110616 A1 | 5/2007 | Blair |
| 2013/0059391 A1 | 3/2013 | Zhang et al. |

OTHER PUBLICATIONS

Simon J. Coutts and Timothy W. Wallace "Heterodiene Cycloadditions: Preparation and Transformations or Some Substituted Pyrano[4,3-b][1]benzopyrans" Tetrahedron vol. 50, No. 40. p. 11755-11780, 1994 (Year: 1994).*

Hideharu Iwasaki, Takashi Kume, Yohsuke Yamamoto and Kin-ya Akiba "Reaction of 4-t-Butyldimethylsiloxy-1-Benzopyrylium Salt With Enol Silyl Ethers and Active Methylenes" Tetrahedron Letters, vol. 28, No. 50, pp. 6355-6358, 1987 (Year: 1987).*

Jake R. Zimmerman, Olivia Johntony, Daniel Steigerwald, Cody Criss, Brian J. Myers, and David H. Kinder; The Synthesis of a New Class of Highly Fluorescent Chromones Via an Inverse-Demand Hetero-Diels-Alder Reaction; Organic Letters, ACS Publications, 2015 American Chemical Society; Received May 14, 2015, Published Jun. 23, 2015; pp. 3256-3259; downloaded by Ohio Northern University on Aug. 25, 2015; http://pubs.acs.org.

Azur Environmental; Microtox Acute Toxicity Test; 1998; pp. 1-23; http://www.coastalbio.com/images/Acute_Overview.pdf.

* cited by examiner

FLUORESCENT COMPOUNDS AS SENSING AGENTS

CROSS-REFERENCE TO RELATED APPLICATIONS

This application claims the benefit of U.S. Provisional Application No. 62/299,321 entitled "Fluorescent Compounds as Sensing Agents" filed on Feb. 24, 2016, which is incorporated by reference herein in its entirety.

FIELD OF THE INVENTION

This invention relates to a new class of fluorophores that, in some instances, shifts emission wavelength upon binding of heavy metal ions. The fluorophores are useful for, for example, detecting the presence of heavy metal ions in water.

BACKGROUND

Over the past decade, there has been a significant interest in fluorescence chemical sensing. This has been fueled by advances in instrumentation and light emitting probes such as fluorophores. Fluorophores, also referred to herein as fluorescent molecules, are molecules that absorb electromagnetic radiation and emit light. The wavelength of the emitted light is impacted by many factors, including the structure of the molecule, the presence of bound ions, and solvent properties. Researchers seek to develop fluorophores that undergo measurable changes in their fluorescence in response to conformational changes or ion binding. These molecules may then be used as probes to image, track, and sense such changes.

Fluorophores typically have limitations and drawbacks. For instance, to be useful as indicators or probes, a fluorophore preferably exhibits a combination of, if not all of, a sufficiently high absorption coefficient and quantum yield to absorb radiation from a radiation source and subsequently fluoresce strongly to allow for detection, an emission frequency that can be discriminated from any background autofluorescence, minimal to no photobleaching, and a large Stokes shift to filter out the excitation light. It is also important that fluorophores be low cost and easy to handle for widespread use in standardly-equipped chemical, physical, and cell biology labs, or for use outside of the lab. Because of these requirements, the development of new, useful fluorophores is a difficult task, especially because there is not a good process or set of criteria available to predict a fluorophore's overall properties.

BRIEF SUMMARY

In some instances, a method may comprise: exposing a substituted chromone according to Compound 1 dissolved in a solvent to a sample, wherein $R_1$ is methyl acetate or methyl (2,2-dimethyl) acetate, $R_2$ is hydroxymethylene, (4-methylphenylsulfonamido)methylene, or ((4-methoxyphenyl)sulfamido)methylene, $R_3$ is hydrogen, methoxy, bromo, chloro, fluoro, methyl, ethyl, or isopropyl, $R_4$ is hydrogen, methoxy, bromo, chloro, fluoro, methyl, ethyl, or isopropyl, and $R_5$ is hydrogen, methoxy, bromo, chloro, fluoro, methyl, ethyl, or isopropyl; taking a fluorescence measurement of the sample after exposure to the substituted chromone; and determining a presence or absence of one or more ions in the sample, a concentration of the one or more ions in the sample, or both based on the fluorescence measurement.

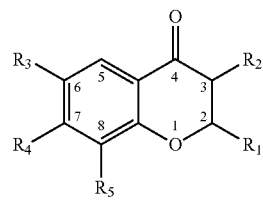

Compound 1

In some instances, a method may comprise: exposing a substituted chromone according to Compound 1 dissolved in a solvent to a sample, wherein $R_1$ is methyl acetate or methyl (2,2-dimethyl) acetate, $R_2$ is hydroxymethylene, (4-methylphenylsulfonamido)methylene, ((4-methoxyphenyl)sulfamido)methylene, or (4-methoxyphenylamido)methylene, $R_3$ is hydrogen, methoxy, bromo, chloro, fluoro, methyl, ethyl, or isopropyl, $R_4$ is hydrogen, methoxy, bromo, chloro, fluoro, methyl, ethyl, and isopropyl, and $R_5$ is hydrogen, methoxy, bromo, chloro, fluoro, methyl, ethyl, or isopropyl; taking a fluorescence measurement of the sample; determining a presence or absence of $Pb^{2+}$ ions in the sample, a concentration of the $Pb^{2+}$ ions in the sample, or both based on the fluorescence measurement; adding a chelating agent to the sample or a source of the sample; and extracting the chelating agent complexed with the $Pb^{2+}$ ions from the sample or the source of the sample.

In some instances, a composition may comprise: Compound 1, wherein $R_1$ is methyl acetate or methyl (2,2-dimethyl) acetate, $R_2$ is hydroxymethylene, (4-methylphenylsulfonamido)methylene, or ((4-methoxyphenyl)sulfamido)methylene, $R_3$ is hydrogen, methoxy, bromo, chloro, fluoro, methyl, ethyl, or isopropyl, $R_4$ is hydrogen, methoxy, bromo, chloro, fluoro, methyl, ethyl, or isopropyl, and $R_5$ is hydrogen, methoxy, bromo, chloro, fluoro, methyl, ethyl, or isopropyl.

DETAILED DESCRIPTION

Figure 1:
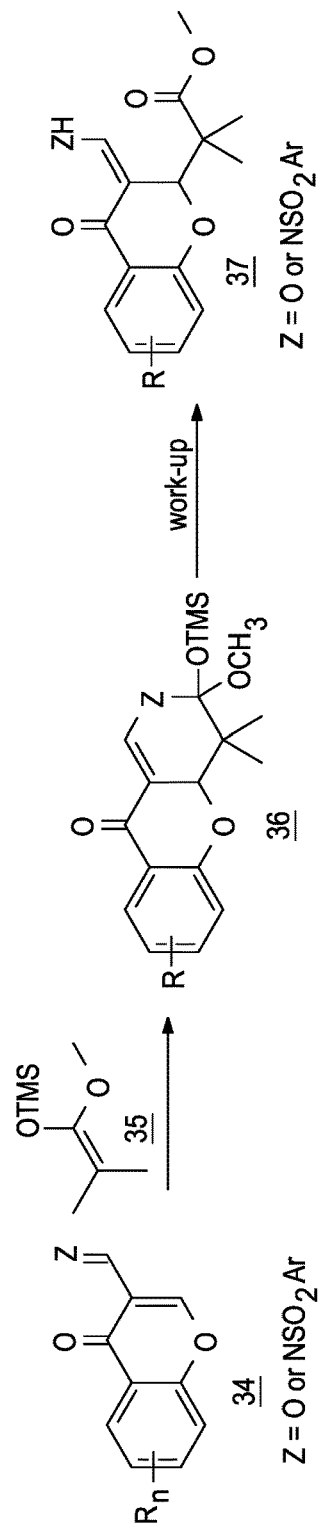
FIG. 1 illustrates an inverse electron demand hetero-Diels-Alder (HDA) reaction useful for producing at least some of the fluorophores described herein.

The present disclosure relates to a new class of fluorophores based on a chromone structure, where the synthesis may include an inverse electron demand hetero-Diels-Alder (HDA) reaction from readily available materials. The structure of the fluorophores is designed with the flexibility to have multiple substituents to the base chromone structure. By altering the chemical composition and location of the substituents, the properties of the substituted chromone may be adjusted including, but not limited to, a peak absorption wavelength, a peak emission wavelength, an ability to chelate to metal ions, and a selectivity for such chelation.

Compound 1 illustrates a general structure for a substituted chromone of the present disclosure. More specifically, Compound 1 has a chromone structure with substitutions in the 2 position ($R_1$), the 3 position ($R_2$), optionally the 6 position ($R_3$), optionally the 7 position ($R_4$), and optionally the 8 position ($R_5$). Accordingly, for Compound 1, $R_1$ may be methyl acetate or methyl (2,2-dimethyl) acetate, $R_2$ may be hydroxymethylene, (4-methylphenylsulfonamido)methylene, ((4-methoxyphenyl)sulfamido)methylene, or (4-methoxyphenylamido)methylene, $R_3$ may be hydrogen, methoxy, bromo, chloro, fluoro, methyl, ethyl, or isopropyl, $R_4$ may be hydrogen, methoxy, bromo, chloro, fluoro, methyl, ethyl, or isopropyl, and $R_5$ may be hydrogen, methoxy, bromo, chloro, fluoro, methyl, ethyl, or isopropyl.

Compound 1

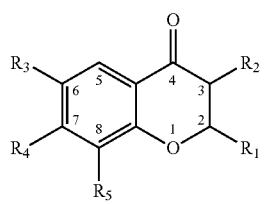

More specifically, Compounds 2-4 provide general structures of the substituted chromones of Compound 1 with the $R_2$ group specified: Compound 2: $R_2$ is hydroxymethylene, and Compound 3: $R_2$ is 4-methylphenylsulfonamido)methylene.

Compound 2

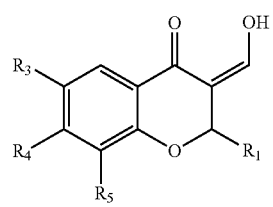

Compound 3

Compound 4

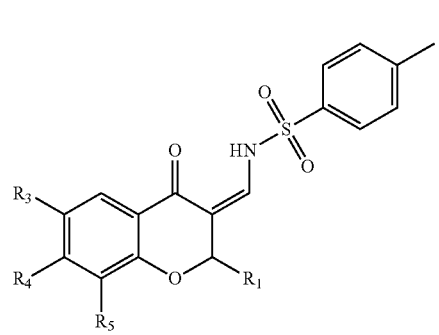

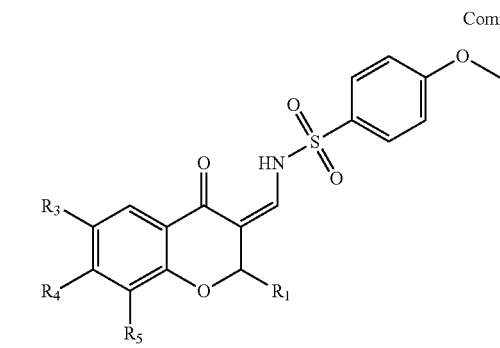

Specific exemplary substituted chromones suitable for use in the methods, kits, systems, and compositions described herein are illustrated in Table 1. It should be noted that the specific embodiments of Table 1 are intended to be exemplary and are in no way limiting to the scope of Compound 1.

TABLE 1

| | Name | Structure |
|---|---|---|
| Compound 5 | (Z)-methyl 2-(3-(hydroxymethylene)-4-oxochroman-2-yl)-2-methylpropanoate | 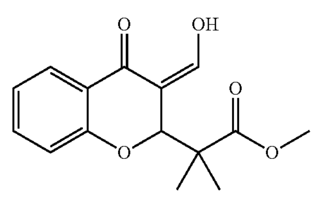 [SMILES: COC(=O)C(C)(C)C1Oc2ccccc2C(=O)/C1=C\O] |
| Compound 6 | (Z)-methyl 2-(6-fluoro-3-(hydroxymethylene)-4-oxochroman-2-yl)-2-methylpropanoate | 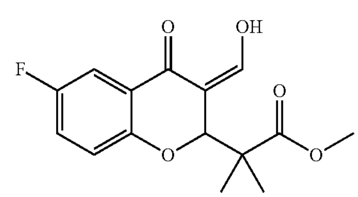 [SMILES: COC(=O)C(C)(C)C1Oc2ccc(F)cc2C(=O)/C1=C\O] |

TABLE 1-continued

| Name | | Structure |
|---|---|---|
| Compound 7 | (Z)-methyl 2-(6-chloro-3-(hydroxymethylene)-4-oxochroman-2-yl)-2-methylpropanoate | 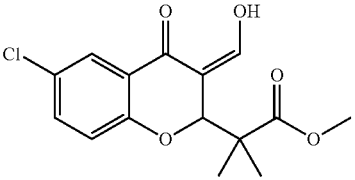 [SMILES: COC(=O)C(C)(C)C1Oc2ccc(Cl)cc2C(=O)/C1=C\O] |
| Compound 8 | (Z)-methy-2-(6-bromo-3-(hydroxymethylene)-4-oxochroman-2-yl)-2-methylpropanoate | 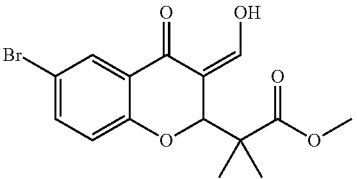 [SMILES: COC(=O)C(C)(C)C1Oc2ccc(Br)cc2C(=O)/C1=C\O] |
| Compound 9 | (Z)-methyl-2-(3-(hydroxymethylene)-6-methyl-4-oxochroman-2-yl)-2-methylpropanoate | 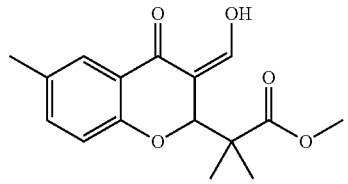 |
| Compound 10 | (Z)-methyl 2-(6-ethyl-3-(hydroxymethylene)-4-oxochroman-2-yl)-2-methylpropanoate | 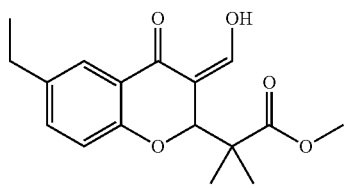 [SMILES: CCc1ccc2c(c1)C(=O)/C(=C\O)C(C(C)(C)C(=O)OC)O2] |
| Compound 11 | (Z)-methyl-2-(3-(hydroxymethylene)-6-methoxy-4-oxochroman-2-yl)-2-methylpropanoate | 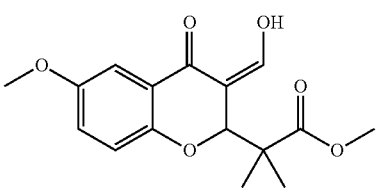 |
| Compound 12 | (Z)-methyl-2-(6-chloro-3-(hydroxymethylene)-7-methyl-4-oxochroman-2-yl)-2-methylpropanoate | 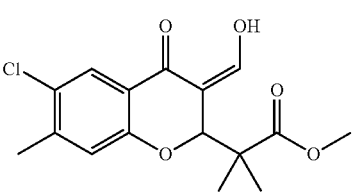 [SMILES: COC(=O)C(C)(C)C1Oc2cc(C)c(Cl)cc2C(=O)/C1=C\O] |
| Compound 13 | (Z)-methyl 2-(6,8-dichloro-3-(hydroxymethylene)-4-oxochroman-2-yl)-2-methylpropanoate | 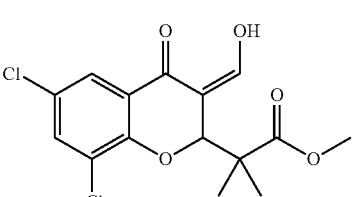 |
| Compound 14 | (Z)-methyl 2-(6,8-dibromo-3-(hydroxymethylene)-4-oxochroman-2-yl)-2-methylpropanoate | 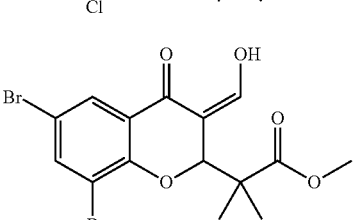 |

TABLE 1-continued

| Name | Structure |
|---|---|
| Compound 15 | (Z)-methyl 2-methyl-2-(3-((4-methylphenylsulfonamido)methylene)-4-oxochroman-2-yl)propanoate |
| Compound 16 | (Z)-methyl 2-(6-fluoro-3-((4-methylphenylsulfonamido)methylene)-4-oxochroman-2-yl)-2-methylpropanoate |
| Compound 17 | (Z)-methyl 2-(6-chloro-3-((4-methylphenylsulfonamido)methylene)-4-oxochroman-2-yl)-2-methylpropanoate |
| Compound 18 | (Z)-methyl 2-(6-bromo-3-((4-methylphenylsulfonamido)methylene)-4-oxochroman-2-yl)-2-methylpropanoate |
| Compound 19 | (Z)-methyl 2-methyl-2-(6-methyl-3-((4-methylphenylsulfonamido)methylene)-4-oxochroman-2-yl)propanoate |

TABLE 1-continued

| Name | | Structure |
|---|---|---|
| Compound 20 | (Z)-methyl 2-(6-ethyl-3-((4-methylphenylsulfonamido)methylene)-4-oxochroman-2-yl)-2-methylpropanoate | 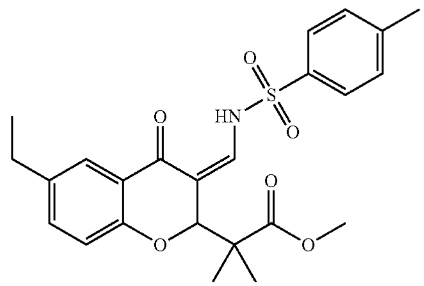 [SMILES: CCc1ccc2c(c1)C(=O)/C(=C\NS(=O)(=O)c1ccc(C)cc1)C(C(C)(C)C(=O)OC)O2] |
| Compound 21 | (Z)methyl-2-(6-isopropyl-3-(((4-methylphenyl)sulfonamido)methylene)-4-oxochroman-2-yl)-2-methylpropanoate | 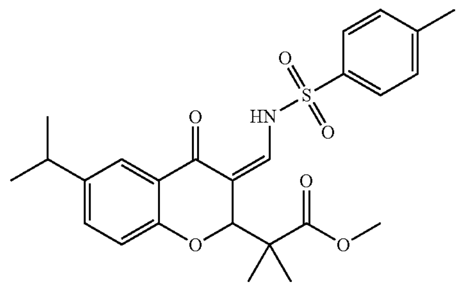 [SMILES: COC(=O)C(C)(C)C1Oc2ccc(C(C)C)cc2C(=O)/C1=C\NS(=O)(=O)c1ccc(C)cc1] |
| Compound 22 | (Z)-methyl-2-(6-methoxy-3-(((4-methylphenyl)sulfonamido)methylene)-4-oxochroman-2-yl)-2-methylpropanoate | 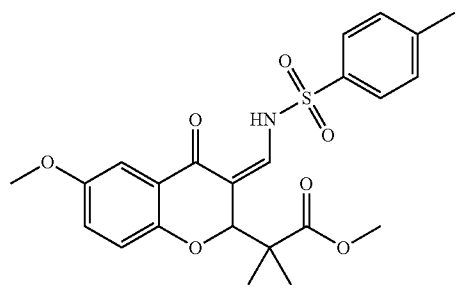 |
| Compound 23 | (Z)methyl-2-(3-(((4-methoxyphenyl)sulfonamido)methylene)-4-oxochroman-2-yl)-2-methylpropanoate | 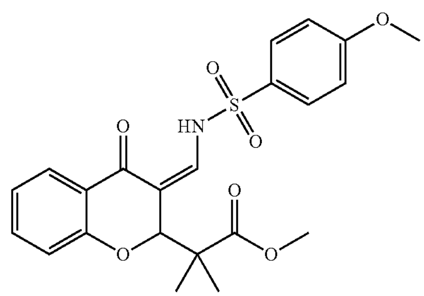 [SMILES: COC(=O)C(C)(C)C1Oc2ccccc2C(=O)/C1=C\NS(=O)(=O)c1ccc(OC)cc1] |
| Compound 24 | (Z)methyl-2-(3-(((4-methoxyphenyl)sulfonamido)methylene)-6-methyl-4-oxochroman-2-yl)-2-methylpropanoate | 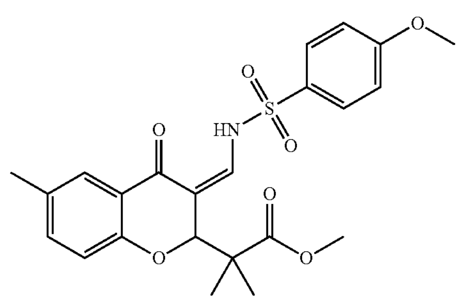 |

TABLE 1-continued

| Name | Structure |
|---|---|
| Compound 25 | (Z)methyl-2-(6-methoxy-3-(((4-methoxyphenyl)sulfonamido)methylene)-4-oxochroman-2-yl)-2-methylpropanoate |
| Compound 26 | (Z)-methyl-2-(6-methoxy-3-(((4-methoxyphenyl)sulfonamido)methylene)-4-oxochroman-2-yl)acetate |

Figure 2:
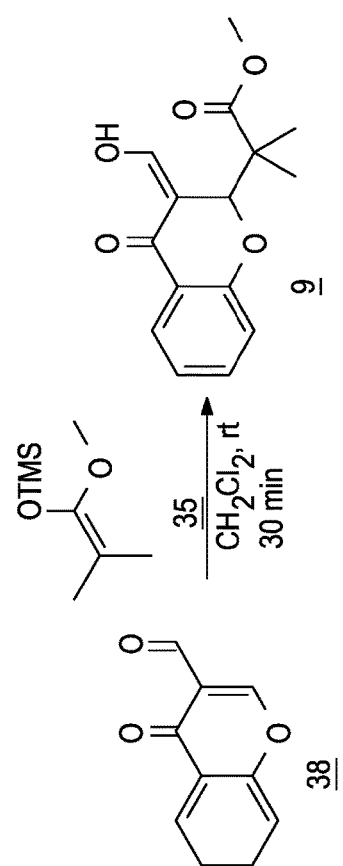
FIG. 2 illustrates an inverse electron demand HDA reaction for producing (Z)-methyl 2-(3-(hydroxymethylene)-4-oxochroman-2-yl)-2-methylpropanoate.

According to various embodiments, the substituted chromones of the present disclosure may be readily synthesized using organic chemistry techniques. FIGS. 1-2 illustrate various exemplary synthetic pathways that may be used to produce substituted chromones. It should be noted that the featured synthetic pathway embodiments are intended to be exemplary and are in no way limiting to the scope of the synthetic pathway suitable for producing substituted chromones described herein.

FIG. 1 illustrates a general inverse-demand hetero-Diels-Alder (HDA) reaction useful for adding the $R_1$ group of Compound 1 to the 2 position of the chromone structure. Compound 34 is a chromone structure having substitution at the 3 position that is the precursor to the $R_2$ group of Compound 1 (e.g., an aldehyde for the $R_2$ group of hydroxymethylene or a sulfonamide for the $R_2$ group of ((4-methylphenylsulfonamido)methylene) or ((4-methoxyphenyl)sulfamido)methylene) and optionally substitution in the aromatic ring of the chromone corresponding to $R_3$, $R_4$, and/or $R_5$, depending on the desired substituted chromone product. Compound 34 is reacted with dimethylsilyl ketene acetal (Compound 35) to produce a Diels-Alder intermediate shown as Compound 36, which has a third ring structure added to the chromone structure. The reaction between Compounds 34 and 35 may be performed at room temperature (or an elevated temperature, e.g., up to about 50° C.) in a solvent like dichloromethane and/or tetrahydrofuran for about 10 minutes to about 2 hours. Upon workup, Compound 37, which correspond to some embodiments of Compound 1, is produced and isolated.

FIG. 2 illustrates a specific inverse-demand hetero-Diels-Alder (HDA) reaction for producing Compound 9, which is (Z)-methyl 2-(3-(hydroxymethylene)-4-oxochroman-2-yl)-2-methylpropanoate. Briefly, 3-formylchromone (Compound 38) is reacted with Compound 35 in dichloromethane for 30 minutes at room temperature and worked up to produce Compound 9.

The substituted chromones of Compound 1 with the $R_2$ group of hydroxymethylene may have a peak absorption wavelength between about 300 nm and about 400 nm and a peak emission wavelength between about 420 nm and about 520 nm. The substituted chromones of Compound 1 with the $R_2$ group of ((4-methylphenylsulfonamido)methylene) or ((4-methoxyphenyl)sulfamido)methylene) may have a peak absorption wavelength between about 330 nm and about 430 nm and a peak emission wavelength between about 450 nm and about 550 nm. The values for the peak absorption wavelength and the peak emission wavelength for specific compounds are provided in Example 1.

In some embodiments, the substituted chromones of the present disclosure may form a complex with ions where complexing with the ions may cause a change in the peak emission wavelength and/or the emission intensity for a specific wavelength of the corresponding fluorescence. One or both of these fluorescent properties may be monitored to determine the presence of ions and/or the concentration of ions in a sample. Determination of the concentration of ions in the sample may be achieved by comparing fluorescent properties (e.g., the amount of and/or change to the peak emission shift and/or emission intensity) to a table, graph, color chart reference, or other mathematical representation (e.g., a mathematical formula) of a known correlation between concentration and the fluorescent properties.

As illustrated in Example 1, the fluorescence of the substituted chromones is in the visible spectrum. Accordingly, the changes in peak emission wavelength may be detected visually upon excitation with a long wavelength UV-source (e.g., a 365 nm source) or other suitable excitation source that excites the substituted chromone, which may be at or near the peak absorption wavelength (e.g., at a wavelength between about 300 nm and about 450 nm). The color emitted may be used qualitatively to determine if a specific ion is present (e.g., Example 8). Alternatively or in combination, the color emitted may be compared to reference samples or a color chart reference for a more quantitative analysis of ion concentration. For example, a color chart reference specific to the substituted chromone color change range may be used in a similar way a color chart reference is used with pH paper to qualitatively and/or quantitatively analyze a color change to pH paper.

Figure 3:
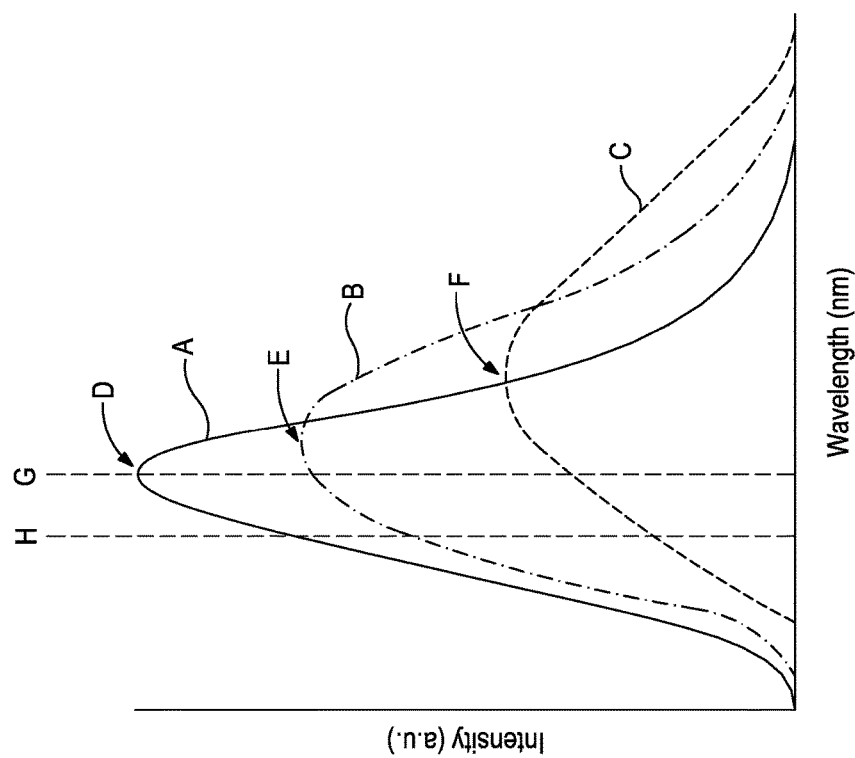
FIG. 3 illustrates three hypothetical emission spectra for a substituted chromone of the present disclosure.

Measuring the emission intensity may be performed in multiple ways as illustrated in FIG. 3 using a fluorimeter such as a photodiode, phototransistor, avalanche photodiode, photoresistor, or a photomultiplier tube. FIG. 3 illustrates three hypothetical emission spectra for a substituted chromone of the present disclosure where Spectra A is the fluorescence spectra with no ions present, Spectra B is the fluorescence spectra with a first concentration of ions present, and Spectra C is the fluorescence spectra with a second concentration of ions present greater than the first concentration. In some instances, the emission intensity may be measured at the peak emission wavelength for each spectrum taken (e.g., at wavelengths corresponding to points D, E, and F of FIG. 3). Alternatively or in combination therewith, the emission intensity may be measured at a specific emission wavelength, which may be the peak emission wavelength substituted chromones without having ions present (e.g., at wavelength G of FIG. 3) or at a specific wavelength where emission intensity varies with varying ion concentration (e.g., at wavelength H of FIG. 3). In some instances, the available hardware may dictate the methods available for implementation. For example, if a detector for a single wavelength or small window of wavelengths is available, analysis according to wavelength H may be required. In some instances, more than one of the foregoing methods may be implemented.

In some instances, the substituted chromones of the present disclosure may form a complex with metal ions. Exemplary metal ions may include, but are not limited to, $Fe^{2+}$, $Fe^{3+}$, $Pb^{2+}$, $Hg^{2+}$, $Zn^{2+}$, $Cd^{2+}$, $Cr^{3+}$, $Mn^{2+}$, and $As^{3+}$, and the like, and any combination thereof. When bound to a metal ion, the peak emission wavelength of the substituted chromones may shift, typically red-shift to longer wavelengths. As described above and as illustrated in Examples 2-5, the change in fluorescence properties (e.g., peak emission wavelength and/or emission intensity) may be correlated to a concentration of the metal ions.

The substituted chromones of Compound 1 may be dissolved or otherwise dispersed in a solvent at any suitable concentration to observe fluorescence visually or detect fluorescence with a fluorimeter, which, in some instances, may be a concentration of about 0.1 micromolar ($\mu$M) to about 5 $\mu$M or higher depending on the substituted chromone. In some embodiments, a kit, a method, or a system may utilize a stock solution of the substituted chromones described herein at a concentration of about 1 $\mu$M to about 5 $\mu$M, where for detection of ions and analysis of fluorescence the stock solution may be diluted with a solvent (which may be the solvent of the stock solution or another solvent miscible therewith).

In some instances, the substituted chromones of the present disclosure with varying R groups may preferentially bind trivalent metal ions over divalent metal ions. For example, in some instances, the substituents of the substituted chromone may be selected so that the resulting compound preferentially chelates with $Fe^{3+}$ over $Fe^{2+}$ as illustrated in Example 4. Such selectivity may be useful in methods, kits, and systems for detecting iron ion concentrations in biological systems. For example, iron is a strong catalyst that plays a central role in functions such as oxygen transport and catalysis. However, when iron is present in high concentrations, the strong catalytic nature of iron results in the formation of high-energy, reactive radical intermediates, such as peroxyl, alkoxyl, and thiyl-peroxyl. The free radical intermediates may then cause cellular damage by oxidizing proteins and altering nucleic acids. Antioxidants may be employed to ameliorate the effects of iron oxidation by finding and binding free radical species. However, antioxidants are rapidly metabolized and excreted and thus cannot be relied upon entirely. Therefore, it is desirable to monitor iron levels if an accurate approximate concentration of iron in the body is desired. In one preferred embodiment, the concentration of iron ions in a biological system may be detected by observing the peak emission wavelength and/or the intensity of emission.

In some embodiments, the substituted chromones of the present disclosure with varying R groups may preferentially bind with specific metal ions. For example, the R groups may be chosen to selectively bind $Pb^{2+}$ or other environmentally relevant ions (e.g., heavy metal ions). Accordingly, some embodiments may involve exposing substituted chromones to a water sample (e.g., drinking water, waste water effluent from a chemical, manufacturing, or nuclear plant, effluent from a water treatment plant, and the like), an extract from a water sample, extracts from soil samples, and the like) and determining the presence or absence of specific metal ions and/or determining a concentration of the specific metal ions. As illustrated in Example 8, Compound 25 may be particularly useful in detecting and measuring the concentration of $Pb^{2+}$. As used herein, the term "extract" refers to the solvent and dissolved/dispersed chemicals after treating a sample with the solvent. For example, a soil sample may be washed with methanol and the methanol extract may be analyzed for ions according to one or more methods described herein.

In addition to the R groups of the substituted chromones being chosen for a desired selectivity to oxidation state or specific ions, the solvent for the substituted chromones may also affect changes to the fluorescent properties, as illustrated in Examples 3, 5, and 6. Exemplary solvents may include, but are not limited to, water, methanol, ethanol, acetic acid, formic acid, acetone, dimethylformamide, acetonitrile, dimethyl sulfoxide, tetrahydrofuran, dichloromethane, ethyl acetate, and miscible combinations thereof. For example, when detecting $Pb^{2+}$, a preferred solvent system may be a mixture of tetrahydrofuran and methanol at a relative ratio of about 2:1 to about 3:1 tetrahydrofuran:methanol. In some instances, the pH of the solvent may be adjusted, which may also affect the changes to the fluorescent properties of the substituted chromones.

The substituted chromones described herein have unique flexibility and tailorability as fluorophores and may be used in a variety of assays and corresponding kits and methods. For example, a kit may include (1) substituted chromones and dissolved in one or more solvents and (2) a set of instructions for analyzing the presence/absence of one or more ions, analyzing the concentration of one or more ions, or analyzing both. Included with the set of instructions, or separate therefrom, may be a table, graph, color chart reference, or other mathematical representation for correlating a change in one or more fluorescence properties to the concentration of one or more ions.

If a method using the substituted chromones described herein detects the presence of ions in a sample, some embodiments may further involve using a chelating agent to extract the ions from the sample or the source of the sample. For example, dimercaprol or dimercaptosuccinic acid may be used for chelating $As^{3+}$, $Hg^{2+}$, or $Pb^{2+}$. Also, ethylenediamine tetraacetic acid calcium disodium versenate, 1,2-dichloroethane, or triethylamine may be used for chelating $Pb^{2+}$. Other chelating agents for the various ions described herein would be readily derived from the art. Further, combinations of chelating agents may be used for extraction of a single ion or extraction of multiple ions. After chelation, the chelated ions may be removed by traditional methods including solvent extraction, centrifugation, and the like.

In some instances, chelation and extraction of ions may be done with the substituted chromones described herein, whether ion detection is performed or not. That is, some embodiments, optionally in conjunction with the fluorescence detection/analysis methods described herein, may involve adding one or more substituted chromones described herein to a sample (e.g., a water sample) and then using solvent extraction (e.g., with 1-octanol) to extract the one or more substituted chromones with the chelated ions to the solvent layer, for example, as illustrated in Example 10.

Embodiments of the present disclosure include, but are not limited to, Embodiment A, Embodiment B, Embodiment C, and Embodiment D.

Embodiment A is a composition comprising: Compound 1, wherein $R_1$ is methyl acetate or methyl (2,2-dimethyl) acetate, $R_2$ is hydroxymethylene, (4-methylphenylsulfonamido)methylene, or ((4-methoxyphenyl)sulfamido)methylene, $R_3$ is hydrogen, methoxy, bromo, chloro, fluoro, methyl, ethyl, or isopropyl, $R_4$ is hydrogen, methoxy, bromo, chloro, fluoro, methyl, ethyl, or isopropyl, and $R_5$ is hydrogen, methoxy, bromo, chloro, fluoro, methyl, ethyl, or isopropyl. In some instances, Embodiment A may further include one or more of the following optional elements: Element 1: wherein Compound 1 is one selected from the group consisting of Compound 2, Compound 3, and Compound 4; Element 2: wherein Compound 1 is one selected from the group consisting of Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25, and Compound 26; Element 3: wherein Compound 1 is a first Compound 1 and the composition further comprises a second Compound 1 that is different than the first Compound 1; Element 4: Element 3 and wherein the first Compound 1 and the second Compound 1 are independently selected from the group consisting of: Compound 2, Compound 3, and Compound 4; Element 5: Element 3 and wherein the first Compound 1 and the second Compound 1 are independently selected from the group consisting of: Compound 5, Compound 6, Compound 7, Compound 8, Compound 9, Compound 10, Compound 11, Compound 12, Compound 13, Compound 14, Compound 15, Compound 16, Compound 17, Compound 18, Compound 19, Compound 20, Compound 21, Compound 22, Compound 23, Compound 24, Compound 25, and Compound 26; Element 6: wherein the composition further comprises a solvent; Element 7: wherein the composition further comprises one or more ions; and Element 8: Element 7 and wherein the one or more ions comprise one or more selected from the group consisting of: $Fe^{2+}$, $Fe^{3+}$, $Pb^{2+}$, $Hg^{2+}$, $Zn^{2+}$, $Cd^{2+}$, $Cr^{3+}$, $Mn^{2+}$, and $As^{3+}$. Exemplary combination of the foregoing elements include, but are not limited to, Element 6 in combination with Element 1, Element 2, Element 3, Element 4, or Element 5; Element 7 and optionally Element 8 in combination with Element 1, Element 2, Element 3, Element 4, or Element 5; and Elements 6 and 7 and optionally Element 8 in combination with Element 1, Element 2, Element 3, Element 4, or Element 5.

Embodiment B is a method comprising: exposing a substituted chromone according to Compound 1 (see Embodiment A optionally including one or more of Elements 1-8) dissolved in a solvent to a sample; taking a fluorescence measurement of the sample after exposure to the substituted chromone; and determining a presence or absence of one or more ions in the sample, a concentration of the one or more ions in the sample, or both based on the fluorescence measurement. In some instances, Embodiment B may further include one or more of the following optional elements: Element 9: wherein the fluorescence measurement is a first fluorescence measurement; wherein the method further comprises taking a second fluorescence measurement of the sample occurs before exposing the substituted chromone; and wherein determining the presence or absence of the one or more ions in the sample, the concentration of the one or more ions in the sample, or both based on a comparison of the first and second fluorescence measurements; Element 10: wherein taking the fluorescence measurement of the sample involves exposing the sample to a 365 nm wavelength source and visually inspecting fluorescence from the sample; Element 11: wherein determining the presence or absence of the one or more ions in the sample, the concentration of the one or more ions in the sample, or both is based on a comparison of the fluorescence measurement and a color chart reference; Element 12: the method further comprising adding a chelating agent to the sample or a source of the sample; and extracting the chelating agent complexed with the one or more ions from the sample or the source of the sample; Element 13: wherein the sample is from drinking water; a waste water effluent from a chemical, manufacturing, or nuclear plant; or an effluent from a water treatment plant; and Element 14: wherein the sample is an extract from a soil sample. Exemplary combination of the foregoing elements include, but are not limited to, Element 13 in combination with one or more of Elements 9-12; Element 14 in combination with one or more of Elements 9-12; Element 9 in combination with one or more of Elements 10-12; Element 10 in combination with one or both of Elements 11 and 12; and Element 11 in combination with Element 12.

Embodiment C is a method comprising: exposing a substituted chromone according to Compound 1 (see Embodiment A and all optional Elements) dissolved in a solvent to a sample; taking a fluorescence measurement of the sample; determining a presence or absence of $Pb^{2+}$ ions in the sample, a concentration of the $Pb^{2+}$ ions in the sample, or both based on the fluorescence measurement; adding a chelating agent to the sample or a source of the sample; and extracting the chelating agent complexed with the $Pb^{2+}$ ions from the sample or the source of the sample. some instances, Embodiment B may further include one or more of the following optional elements: Element 9; Element 10; Element 11; Element 13; Element 14; Element 15: wherein the chelating agent is one or more selected from the group consisting of: dimercaproll, dimercaptosuccinic acid, ethylenediamine tetraacetic acid calcium disodium versenate, 1,2-dichloroethane, and trimethylamine; and Element 16: wherein the solvent comprises one or more selected from the group consisting of: methanol and tetrahydrofuran. Exemplary combination of the foregoing elements include, but are not limited to, Element 13 in combination with one or more of Elements 9, 10, 11, 15, or 16; Element 14 in combination with one or more of Elements 9, 10, 11, 15, or 16; Element 9 in combination with one or more of Elements 10, 11, 15, or 16; Element 10 in combination with one or more of Elements 11, 15, or 16; Element 11 in combination with one or both of Elements 15 and 16; and Elements 15 and 16 in combination.

Embodiment D is a kit comprising the composition of Embodiment A optionally including one or more of Elements 1-8; and a correlation between a presence or absence of one or more ions in the sample, a concentration of the one or more ions in the sample, or both and a fluorescence measurement (e.g., a table, a graph, a color chart reference, or a mathematical representation for the correlation). Optionally, the kit may further include one or more of: a fluorimeter, a light source (e.g., a 365 nm wavelength source), a solvent separate from the composition, and dilution equipment (e.g., a graduated cylinder, a pipette, or other fluid measurement tool).

The following examples are given to illustrate the present disclosure. It should be understood, however, that the present disclosure is not to be limited to the specific conditions or details described in these examples.

EXAMPLES

Example 1

Table 2 provides a peak absorption wavelength ($\lambda_{abs}$ maximum), peak emission wavelength ($\lambda_{em}$ maximum), a fluorescent quantum yield ($\Phi_F$), and a synthesis yield for the various compounds. The synthesis yield is based on the synthetic pathway illustrated in FIG. 1.

TABLE 2

| | $\lambda_{abs}$ maximum (nm) | $\lambda_{em}$ maximum (nm) | $\Phi_F$ (%) | Synthesis Yield (%) |
|---|---|---|---|---|
| Compound 5 | 362 | 446 | 6* | 77 |
| Compound 6 | 364 | 486 | 2* | 87 |
| Compound 11 | 383 | 482 | 20* | 82 |
| Compound 14 | 371 | 451 | 3* | 72 |
| Compound 15 | 358 | 479 | 37* | 78 |
| Compound 16 | 367 | 492 | 33* | 90 |
| Compound 17 | 367 | 483 | 39* | 80 |
| Compound 18 | 343 | 483 | 34* | 88 |
| Compound 19 | 367 | 492 | 70* | 80 |
| Compound 19 | 380 | 468 | 8** | 80 |
| Compound 19 | 364 | 479 | 27*** | 80 |
| Compound 20 | 370 | 490 | 73* | 70 |
| Compound 20 | 369 | 496 | 16** | 70 |
| Compound 20 | 364 | 481 | 30*** | 70 |
| Compound 21 | 368 | 490 | 71* | 93 |
| Compound 22 | 390 | 529 | 66* | 97 |
| Compound 23 | 358 | 479 | 38* | 72 |
| Compound 24 | 367 | 492 | 72* | 76 |
| Compound 25 | 392 | 527 | 69* | 77 |
| Compound 26 | 386 | 529 | 67* | 72 |

The solvent is *dichloromethane, acetonitrile, or *cyclohexane.

Example 2

Figure 5:
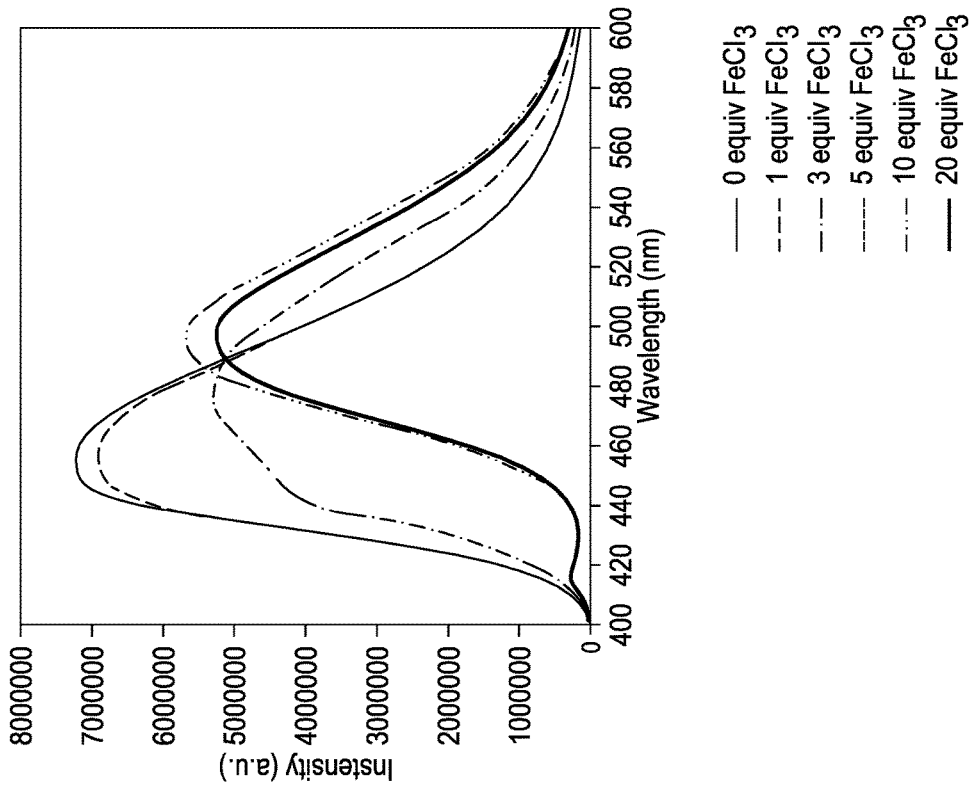
FIG. 5 illustrates the emission spectra spectrum of a substituted chromone (Compound 20 of Table 1) with increasing amounts of $Fe^{3+}$ ions.
Figure 4:
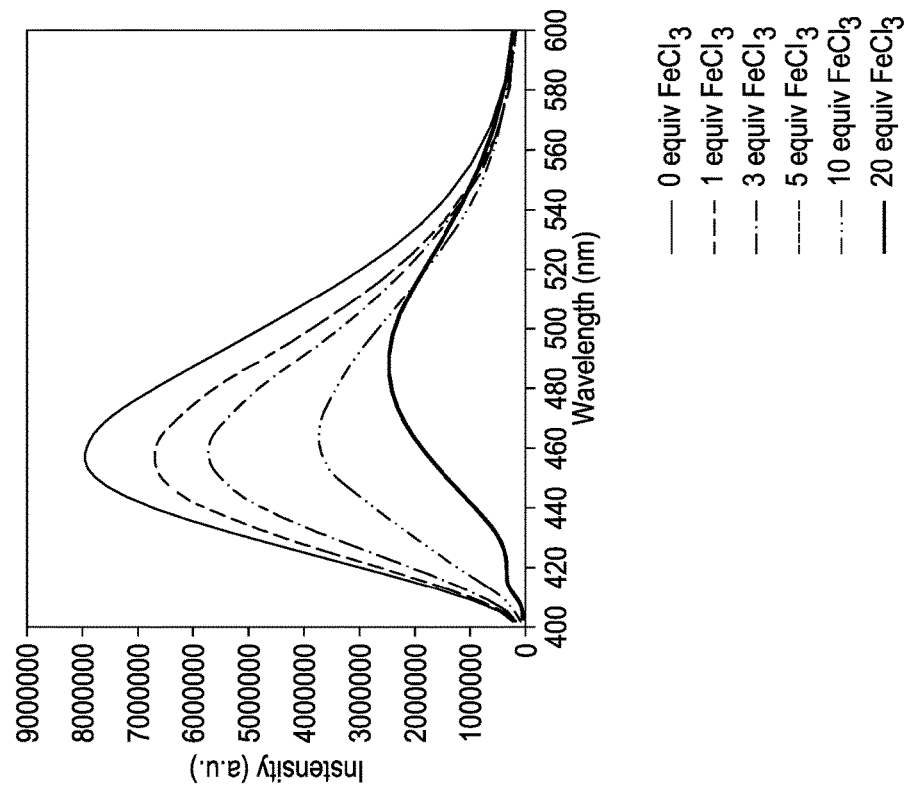
FIG. 4 illustrates the emission spectra of a substituted chromone (Compound 11 of Table 1) with increasing amounts of $Fe^{3+}$ ions.

Two substituted chromones (Compound 11 and Compound 20) were dissolved in methanol and exposed to varying amounts of $FeCl_3$ (i.e., $Fe^{3+}$). FIG. 4 illustrates the shift in emission spectrum of Compound 11 with increasing amounts of $Fe^{3+}$ ions. With about 10 equivalents of $Fe^{3+}$ ions, the shift in emission spectrum is saturated, with a total of about a 30 nm red-shift in peak emission wavelength. FIG. 5 illustrates the shift in emission spectrum of Compound 20 with increasing amounts of $Fe^{3+}$ ions. With about 10 equivalents of $Fe^{3+}$ ions, the shift in emission spectrum is saturated, with a total of about a 50 nm red-shift in peak emission wavelength. Interestingly, when this experiment is repeated in a 1:1 methanol:water as the solvent, Compound 11 still exhibits a red-shift in peak emission wavelength while Compound 20 does not.

Further, in both FIGS. 4 and 5 the intensity of the peak emission wavelength changes with changing metal ion concentration, which may be used in conjunction with or separate from the red-shift in peak emission wavelength in determining the concentration of metal ions.

Example 3

Compound 11 was dissolved in various solvents and then exposed to varying amounts of $FeCl_3$ (i.e., $Fe^{3+}$). In polar aprotic solvents such as tetrahydrofuran, acetonitrile, and acetone, the peak emission wavelength of Compound 11 did not exhibit an appreciable red-shift. In polar protic solvents like water, methanol, and mixtures thereof, the peak emission wavelength of Compound 11 exhibited an appreciable red-shift.

Example 4

Figure 6:
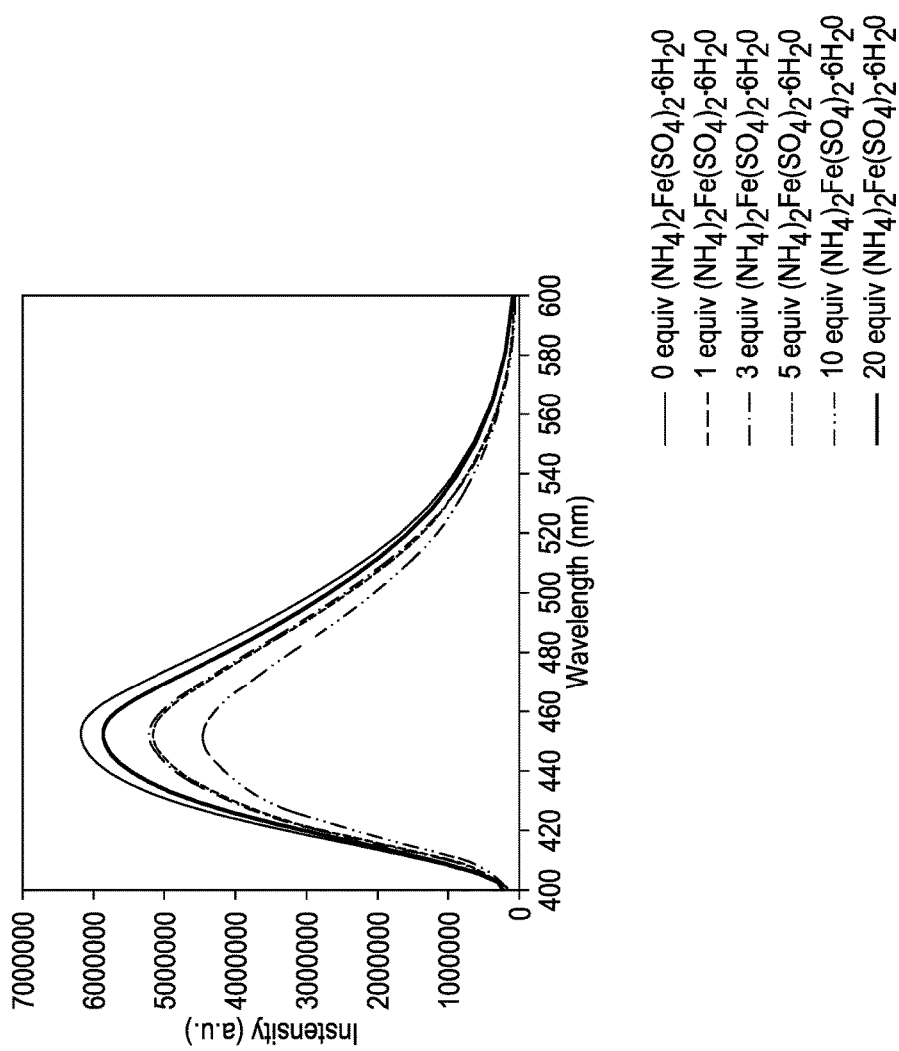
FIG. 6 illustrates the emission spectra of a substituted chromone (Compound 11 of Table 1) with increasing amounts of $Fe^{2+}$ ions.
Figures 7, 8:
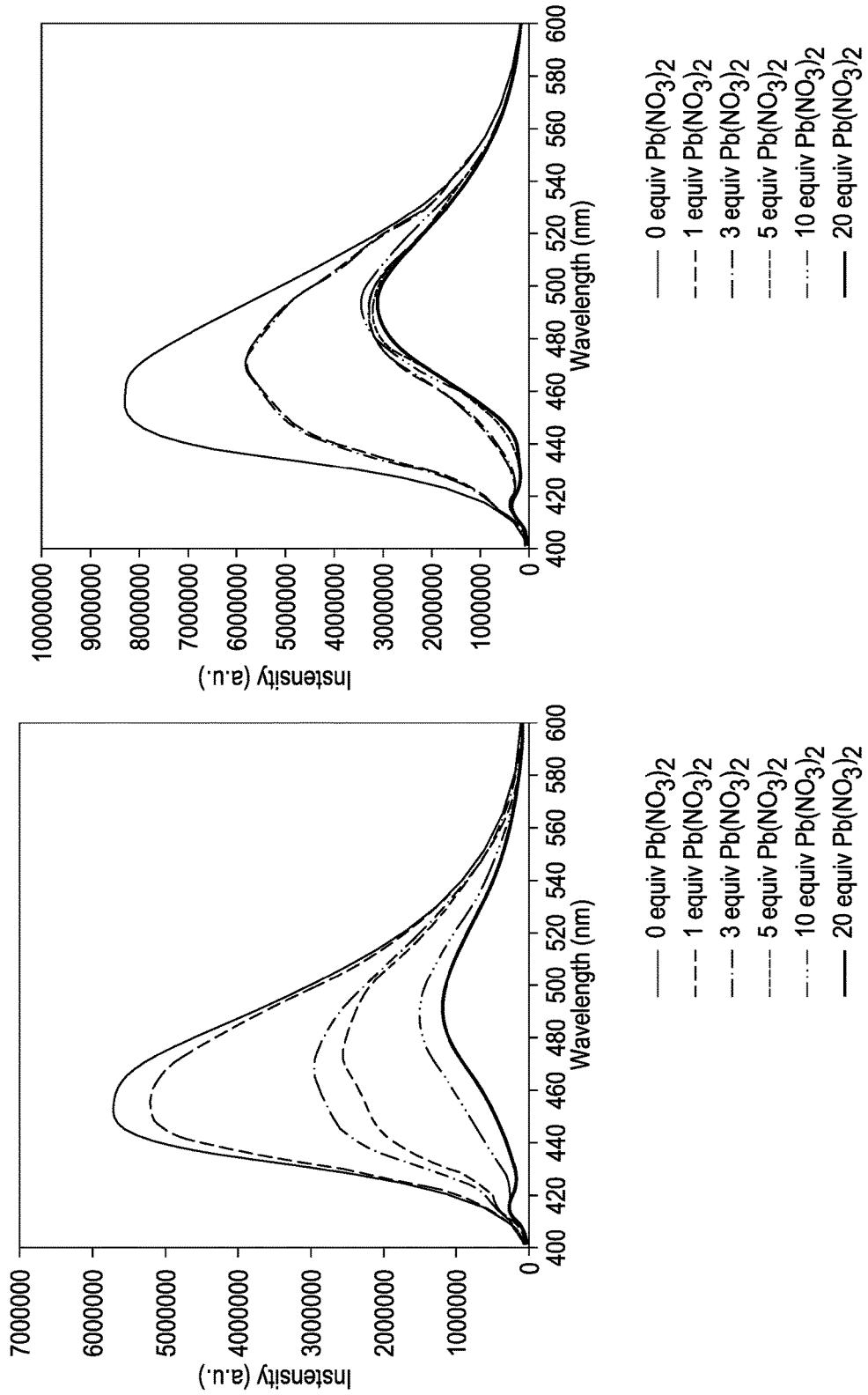
FIGS. 7-10 illustrate the emission spectra of a substituted chromone (Compound 20 of Table 1) in the presence of $Pb^{2+}$ with different solvents (FIG. 7 in methanol, FIG. 8 in 1:1 tetrahydrofuran:methanol, FIG. 9 in 3:1 tetrahydrofuran:methanol, FIG. 10 in tetrahydrofuran).
Figures 9, 10:
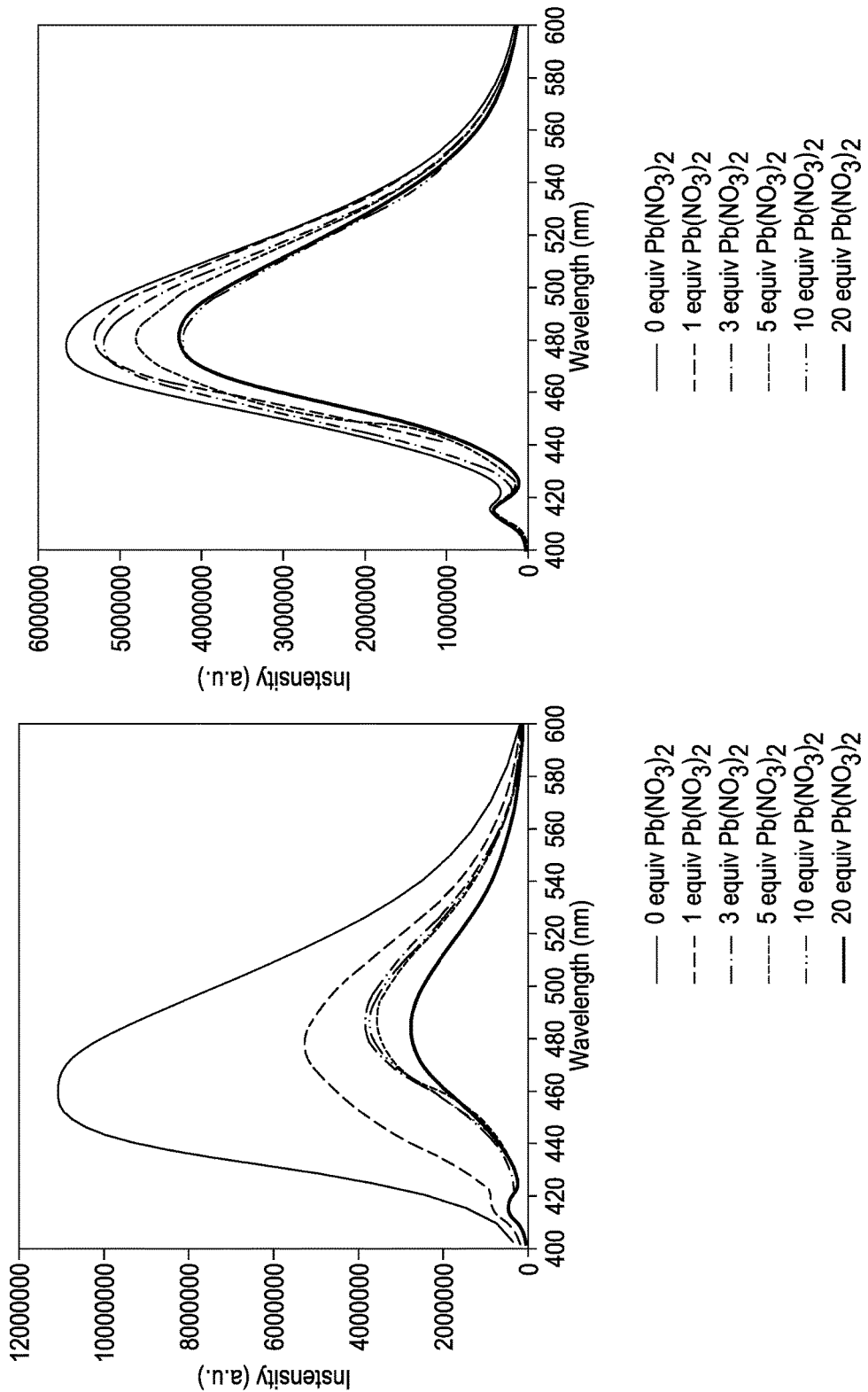

Compound 11 was dissolved in methanol and then exposed to varying amounts of $FeCl_3$ (i.e., $Fe^{3+}$) or $(NH_4)_2Fe(SO_4)_2 \cdot 6H_2O$ (i.e., $Fe^{2+}$). As shown in FIGS. 4 and 6, the peak emission wavelength of Compound 11 undergoes a significant red-shift in the presence of $Fe^{3+}$ (FIG. 4) but does not exhibit appreciable shift emission wavelength in the presence of $Fe^{2+}$ (FIG. 6). Therefore, Compound 11 may be used to detect $Fe^{3+}$ while in the presence of $Fe^{2+}$. However, both FIGS. 4 and 6 exhibit an intensity decrease for the peak emission wavelength with increasing metal ion concentration, which may be used in conjunction with or separate from the red-shift in peak emission wavelength in determining the concentration of metal ions.

Example 5

Compound 20 was dissolved in methanol and then exposed to varying amounts of $Pb(NO_3)$ (i.e., $Pb^{2+}$). As shown in FIGS. 7-10, the peak emission wavelength of Compound 20 undergoes a red-shift and intensity decrease to differing degrees in the presence of $Pb^{2+}$ depending on the solvent (FIG. 7 in methanol, FIG. 8 in 1:1 tetrahydrofuran:methanol, FIG. 9 in 3:1 tetrahydrofuran:methanol, FIG. 10 in tetrahydrofuran). In methanol, the shift in peak emission wavelength maxes out at 10 equivalents but no appreciable shift at 1 equivalent. In contrast, a mixed tetrahydrofuran/methanol does have an appreciable shift at 1 equivalent but a max shift at a much lower concentration (about 5 equivalents for 1:1 tetrahydrofuran:methanol and about 3 equivalents for 3:1 tetrahydrofuran:methanol). Further, in THF alone, there is no appreciable shift in peak emission wavelength. Therefore, a kit, method, system, or the like may utilize a specific solvent system for detection of lead or other Ions. Alternatively, and especially where the metal ion concentration is unknown, a kit, method, system, or the like may utilize a series of solvent systems in parallel to determine a concentration of metal ions.

Example 6

Figures 11, 12:
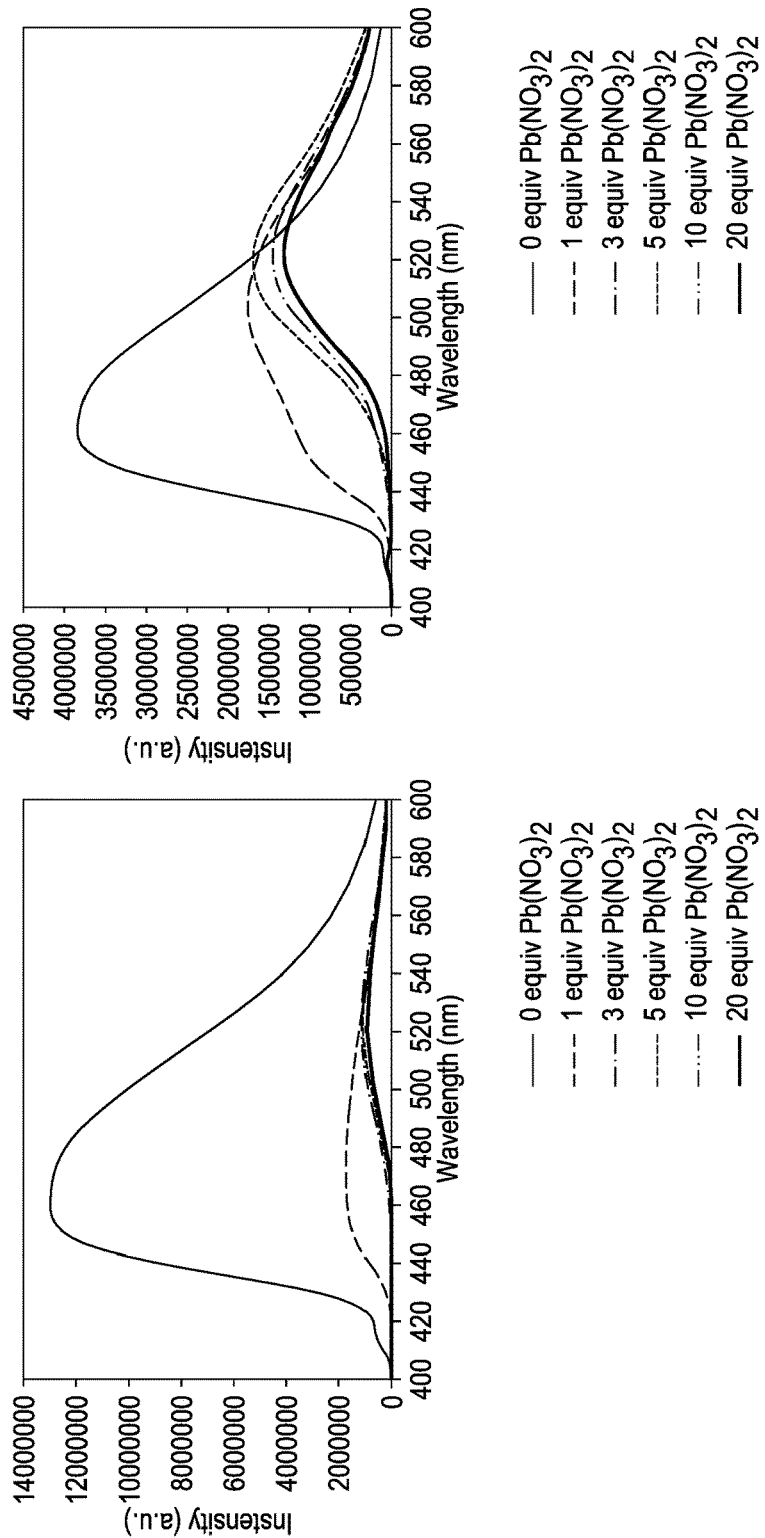
FIGS. 11-12 illustrate the emission spectra of a substituted chromone (Compound 25 of Table 1) in the presence of $Pb^{2+}$ with different solvents (FIG. 11 in 3:1 tetrahydrofuran:methanol and FIG. 12 in 2:1 tetrahydrofuran:methanol).

A 5 μM sample of Compound 25 in 3:1 tetrahydrofuran:methanol or 2:1 tetrahydrofuran:methanol was prepared and exposed to varying amounts of $Pb(NO_3)_2$ (i.e., $Pb^{2+}$) dissolved in deionized water. As shown in FIGS. 11-12 using an excitation wavelength of 370 nm, the peak emission wavelength of Compound 25 undergoes a red-shift and intensity decrease to differing degrees in the presence of $Pb^{2+}$ depending on the solvent (FIG. 11 in 3:1 tetrahydrofuran:methanol and FIG. 12 in 2:1 tetrahydrofuran:methanol). Further, the overall red shift in the peak emission wavelength is very similar, which visually changes the fluorescence from blue to green.

Example 7

The detection limit $Pb(NO_3)_2$ (i.e., $Pb^{2+}$) for Compound 25 in 3:1 tetrahydrofuran:methanol was tested by exposing samples of 5 μM Compound 25 to ever decreasing concentrations of $Pb(NO_3)_2$ dissolved in deionized water. A detection limit where the visual change from blue to green was determined to be about 2.5 μM to about 5 μM $Pb^{2+}$, where the use of a fluorimeter would allow for detection of even lower concentrations. The color change observed was almost instantaneous, which illustrates that kits and methods using the substituted chromones described herein provide quick results.

Example 8

Compound 25 shows a selectivity for $Pb^{2+}$ ions over other heavy metal ions. Compound 25 was dissolved in 3:1 tetrahydrofuran:methanol and then exposed to varying amounts of $Zn/SO_4$ (i.e., $Zn^{2+}$), $(NH_4)_2Fe(SO_4)_2.6H_2O$ (i.e., $Fe^{2+}$), $Fe_2O_3$ (i.e., $Fe^{3+}$), $CuSO_4$ (i.e., $Cu^{2+}$), or $Pb(NO_3)_2$ (i.e., $Pb^{2+}$) each in deionized water. Upon visual inspection when excited at 365 nm, the sample exposed to $Pb^{2+}$ turned green while all other samples remained blue. Similar results were observed when Compound 20 was tested. This example illustrates that the substituted chromones of the present disclosure may be chosen to exhibit a fluorescence color change in the presence of specific ions, which may be useful in kits and methods for detecting specific ions and their concentration in samples like drinking water.

Example 9

A 40 mM solution of $Pb(NO_3)_2$ (i.e., $Pb^{2+}$) was prepared in tap water and then diluted with 3:1 tetrahydrofuran:methanol to a lead concentration of 133 μM. The resultant sample was added to solutions of 5 μM sample of Compound 25 in 3:1 tetrahydrofuran:methanol. A detection limit where the visual change from blue to green was determined to be about 2.5 μM to about 5 μM $Pb^{2+}$, where the use of a fluorimeter would allow for detection of even lower concentrations. This example illustrates that the lead detection can be performed using tap water, which includes a variety of other ions.

Example 10

A 3 mM $Pb(NO_3)_2$ sample was prepared in deionized water and Compound 25 was added to give a green fluorescence. The lead was then extracted from the water using either 1-octanol or 2-octanol each with 1 equivalent (relative to Compound 25) of triethylamine, which turned the octanol portion green. After washing thrice with 1-octanol, 99% of the $Pb^{2+}$ had been extracted from the water. After washing twice with 2-octanol, 83% of the $Pb^{2+}$ had been extracted from the water.

Example 11

A lead-free soil sample was collected, placed into a Buchner funnel, and soaked with 1 mL of 0.15 M $Pb(NO_3)_2$ in water to introduce lead to the soil. As a control sample, the same was performed with the lead-free soil without exposure to $Pb^{2+}$. After soaking, the soil samples were washed with 50 mL of methanol. A sample from each filtrate was diluted in 3:1 tetrahydrofuran:methanol and exposed to Compound 25. The extract from the soil sample exposed to $Pb^{2+}$ exhibited a color change from blue to green. At the same dilution amount, the soil sample not exposed to $Pb^{2+}$ exhibited no color change. This example illustrates that the substituted chromones described herein may be useful in detecting ions from soil extracts.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present invention. It is noted that, as used in this specification and the appended claims, the singular forms "a," "an," and "the," include plural references unless expressly and unequivocally limited to one reference. As used herein, the term "include" and its grammatical variants are intended to be non-limiting, such that recitation of items in a list is not to the exclusion of other like items that can be substituted or added to the listed items.

Any patent, patent application, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A method comprising:
exposing a substituted chromone according to Compound 1 dissolved in a solvent to a sample, wherein $R_1$ is methyl acetate or methyl (2,2-dimethyl) acetate, $R_2$ is hydroxymethylene, (4-methylphenylsulfonamido)methylene, or ((4-methoxyphenyl)sulfamido)methylene, $R_3$ is hydrogen, methoxy, bromo, chloro, fluoro, methyl, ethyl, or isopropyl, $R_4$ is hydrogen, methoxy, bromo, chloro, fluoro, methyl, ethyl, or isopropyl, and $R_5$ is hydrogen, methoxy, bromo, chloro, fluoro, methyl, ethyl, or isopropyl,

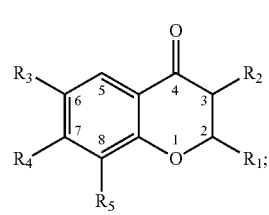

Compound 1 taking a fluorescence measurement of the sample after exposure to the substituted chromone; and determining a presence or absence of one or more ions in the sample, a concentration of the one or more ions in the sample, or both based on the fluorescence measurement.

2. The method of claim 1, wherein the fluorescence measurement is a first fluorescence measurement; wherein the method further comprises taking a second fluorescence measurement of the sample occurs before exposing the substituted chromone; and wherein determining the presence or absence of the one or more ions in the sample, the concentration of the one or more ions in the sample, or both based on a comparison of the first and second fluorescence measurements.

3. The method of claim 1, wherein taking the fluorescence measurement of the sample involves exposing the sample to a 365 nm wavelength source and visually inspecting fluorescence from the sample.

4. The method of claim 1, wherein determining the presence or absence of the one or more ions in the sample, the concentration of the one or more ions in the sample, or both is based on a comparison of the fluorescence measurement and a color chart reference.

5. The method of claim 1 further comprising:
adding a chelating agent to the sample or a source of the sample; and
extracting the chelating agent complexed with the one or more ions from the sample or the source of the sample.

6. The method of 1, wherein the one or more ions comprise one or more selected from the group consisting of: $Fe^{2+}$, $Fe^{3+}$, $Pb^{2+}$, $Hg^{2+}$, $Zn^{2+}$, $Cd^{2+}$, $Cr^{3+}$, $Mn^{2+}$, and $As^{3+}$.

7. The method of claim 1, wherein the sample is from drinking water; a waste water effluent from a chemical, manufacturing, or nuclear plant; or an effluent from a water treatment plant.

8. The method of claim 1, wherein the sample is an extract from a soil sample.

9. A method comprising:
exposing a substituted chromone according to Compound 1 dissolved in a solvent to a sample, wherein $R_1$ is methyl acetate or methyl (2,2-dimethyl) acetate, $R_2$ is hydroxymethylene, (4-methylphenylsulfonamido)methylene, ((4-methoxyphenyl)sulfamido)methylene, or (4-methoxyphenylamido)methylene, $R_3$ is hydrogen, methoxy, bromo, chloro, fluoro, methyl, ethyl, or isopropyl, $R_4$ is hydrogen, methoxy, bromo, chloro, fluoro, methyl, ethyl, and isopropyl, and $R_5$ is hydrogen, methoxy, bromo, chloro, fluoro, methyl, ethyl, or isopropyl, Compound 1

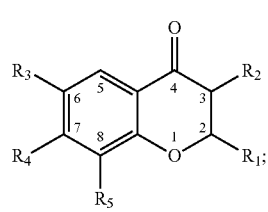

taking a fluorescence measurement of the sample;
determining a presence or absence of $Pb^{2+}$ ions in the sample, a concentration of the $Pb^{2+}$ ions in the sample, or both based on the fluorescence measurement;

adding a chelating agent to the sample or a source of the sample; and
extracting the chelating agent complexed with the $Pb^{2+}$ ions from the sample or the source of the sample.

10. The method of claim 9, wherein Compound 1 is

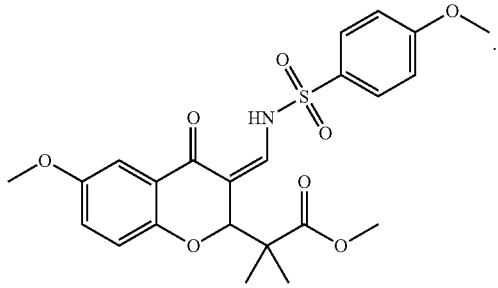

11. The method of claim 9, wherein Compound 1 is

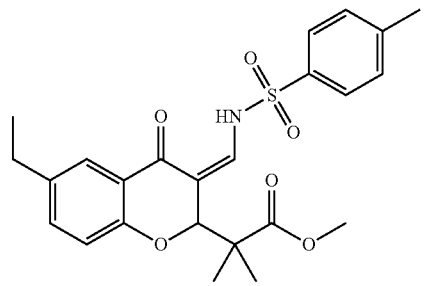

12. The method of claim 9, wherein the chelating agent is one or more selected from the group consisting of: dimercaproll, dimercaptosuccinic acid, ethylenediamine tetraacetic acid calcium disodium versenate, 1,2-dichloroethane, and trimethylamine.

13. The method of claim 9, wherein the solvent comprises one or more selected from the group consisting of: methanol and tetrahydrofuran.

14. The method of claim 9, wherein the fluorescence measurement is a first fluorescence measurement; wherein the method further comprises taking a second fluorescence measurement of the sample occurs before exposing the substituted chromone; and wherein determining the presence or absence of the one or more ions in the sample, the concentration of the one or more ions in the sample, or both based on a comparison of the first and second fluorescence measurements.

15. The method of claim 9, wherein taking the fluorescence measurement of the sample involves exposing the sample to a 365 nm wavelength source and visually inspecting fluorescence from the sample.

16. The method of claim 9, wherein the sample is from drinking water, a waste water effluent from a chemical, manufacturing, or nuclear plant, or an effluent from a water treatment plant.

17. The method of claim 9, wherein the sample is an extract from a soil sample.

* * * * *